United States Patent
Afzali-Ardakani et al.

(10) Patent No.: US 6,963,080 B2
(45) Date of Patent: Nov. 8, 2005

(54) THIN FILM TRANSISTORS USING SOLUTION PROCESSED PENTACENE PRECURSOR AS ORGANIC SEMICONDUCTOR

(75) Inventors: Ali Afzali-Ardakani, Yorktown Heights, NY (US); Tricia L Breen, Hopewell Junction, NY (US); Christos D Dimitrakopoulos, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 105 days.

(21) Appl. No.: 10/300,630

(22) Filed: Nov. 20, 2002

(65) Prior Publication Data

US 2003/0136964 A1 Jul. 24, 2003

Related U.S. Application Data

(60) Provisional application No. 60/333,312, filed on Nov. 26, 2001.

(51) Int. Cl.[7] .............................................. H01L 51/30
(52) U.S. Cl. ..................... 257/40; 257/66; 257/E51.006
(58) Field of Search ............................. 257/40, 66, 72, 257/E51.006; 438/99

(56) References Cited

U.S. PATENT DOCUMENTS

| | | | |
|---|---|---|---|
| 5,946,551 A | 8/1999 | Dimitrakopoulos et al. | .. 438/99 |
| 5,981,970 A | 11/1999 | Dimitrakopoulos et al. | .. 257/40 |
| 6,207,472 B1 | 3/2001 | Callegari et al. ............ | 438/99 |
| 6,335,539 B1 * | 1/2002 | Dimitrakopoulos et al. | .. 257/40 |
| 6,528,816 B1 * | 3/2003 | Jackson et al. ............... | 257/40 |
| 6,545,291 B1 * | 4/2003 | Amundson et al. .......... | 257/40 |
| 6,603,139 B1 * | 8/2003 | Tessler et al. ................ | 257/40 |
| 6,621,098 B1 * | 9/2003 | Jackson et al. ............... | 257/40 |
| 2003/0054586 A1 * | 3/2003 | Shlein et al. ................. | 438/99 |

FOREIGN PATENT DOCUMENTS

| EP | 1041652 A2 * | 10/2000 | ........... H01L/51/20 |
|---|---|---|---|

OTHER PUBLICATIONS

Bladon et al., "*Ethyl and Methyl Thioxoacetates, Dienophilic Thioaldehydes Formed from sulphenyl Chlorides by 1,2–Elimination*", J. Chem. Soc. Perkin Trans. I, 1985, p. 1541–1545.

Kirby et al., "*The Transient Dienophile Diethyl Thioxomalonate and its S–Oxide (sulphine Formed by Retro–Diels–Alder Cleavage Reactions*", J. Chem. Soc. Perkin Trans. I, 1990, pp. 3175–3181.

Garnier et al., "*Structural Basis for High Carrier Mobility in Conjugated Oligomers*", Synthetic Metals, vol. 45, pp. 163–171, 1991.

(Continued)

*Primary Examiner*—Stephen W. Smoot
(74) *Attorney, Agent, or Firm*—Ohlandt, Greeley, Ruggiero & Perle, L.L.P.; Daniel P. Morris, Esq.; IBM Corporation

(57) ABSTRACT

The present invention describes thin film transistors in which the active channel layer is a thin film of a polycyclic aromatic compound, such as, pentacene, prepared by solution processing a soluble precursor of the polycyclic aromatic compound on a substrate followed by heating to a moderate temperature to convert the precursor back to the polycyclic aromatic compound. The soluble precursors of the polycyclic aromatic compounds are organic solvent-soluble Diels-Alder adducts of polycyclic aromatic compounds, such as, oligothiophene, perylene, benzo[ghi] perylene, coronene and a polyacene with a variety of dienophiles that contain at least one heteroatom. The Diels-Alder adducts can be converted back to pentacene by retro-Diels-Alder reaction at moderate (60–250° C.) temperatures both in bulk, in solution or as thin-films.

23 Claims, 8 Drawing Sheets

OTHER PUBLICATIONS

Herwig et al., "*A Soluble Pentacene Precursor: Synthesis, Solid–State Conversion into Pentacene and Application in a Field–Effect Transistor*", Advanced Materials, 1999, vol. 11, No. 6, p. 480–483.

Dimitrakopoulos et al., "*Molecular Beam Deposited Thin Films of Pentacene for Organic Field Effect Transistor Applications*", J. Appl. Phys., vol. 80, pp. 2501–2508, Aug. 1996.

Freer et al., "*Generation of a Thioaldehyde S–Oxide (Sulphine) by Retro–Diels–Alder Reactions*", J. Chem. Soc., Chem. Commun. 1987, pp. 718–719.

Paul F. Vogt and Marvin J. Miller, "*Development and Applications of Amino Acid Derived Chiral Acylnitroso Hetero Diels–Alder Reactions*", Tetrahedron, vol. 54, pp. 1317–1348 (1998).

Bao et al., "*Soluble and Processable Regioregular Poly(3–Hexylthiophene) for Thin Film Field–Effect Transistor Applications with High Mobility*", Appl. Phys. Lett., vol. 69, pp. 4108–4110, Dec. 1996.

Bao et al., "*Organic Field–Effect Transistors with High Mobility Based on Copper Phthalocyanine*", Appl. Phys. Lett., vol. 69, pp. 3066–3068, Nov. 1996.

Klauk et al., "*Pentacene Organic Thin–Film Transistors and ICs*", Solid State Technology, Mar. 2000, pp. 63–67.

\* cited by examiner

THIN FILM TRANSISTORS USING SOLUTION PROCESSED PENTACENE PRECURSOR AS ORGANIC SEMICONDUCTOR

This application claims priority from Provisional Application Ser. No. 60/333,312 filed on Nov. 26, 2001.

This application is related to U.S. application Ser. No. 10/300,645 entitled "Hetero Diets-Alder adducts of Pentacene as Soluble Precursors of Pentacene," filed herewith on the same day, cross-referenced and incorporated herein by reference.

BACKGROUND OF THE INVENTION

1. Field of Invention

The present invention relates to the application of a solution processed polycyclic aromatic compound precursors as an organic semiconducting material in thin film transistors. More particularly, present invention relates to a pentacene precursor that is a hetro Diels-Alder adduct of pentacene with heterodienophiles having at least one heteroatom selected from N, O, or sulfur. These adducts are highly soluble in common organic solvents and can be easily converted back to pentacene in solid state by heating at moderate temperatures.

2. Background of the Invention

Thin-film transistors (TFT) and other electronic devices using organic semiconductors are emerging as alternatives to established methods using amorphous silicon ($\alpha$-Si:H) as the semiconductor.

Amorphous silicon ($\alpha$-Si:H) is typically used in thin film field-effect transistors in many applications including liquid crystal displays. In the past decade significant efforts have been directed towards development of organic semiconductors to replace amophous silicon in low-end applications. The organic materials provide the ability to produce these devices bypassing the expensive steps associated with silicon processing.

Other advantages of organic semiconductors include low temperature processing combined with ease of deposition of thin films of these materials over large areas. These processing characteristics enable the fabrication of organic thin film transistors (OTFT) on plastic substrates, which offer light weight, mechanical flexibility and ruggedness.

A variety of organic materials have been designed, synthesized and characterized as p-type semiconductors (majority carriers are holes). Organic thin film transistor (TFT) devices have been made using such materials. Among them, thiophene oligomers have been proposed as semiconducting materials in Garnier et al., "Structural basis for high carrier mobility in conjugated oligomers" *Synth. Met.*, Vol., 45, p. 163 (1991). Benzodithiophene dimers are proposed as organic semiconductor materials in Liquindanum, J. et al., "Benzodithiophene rings as semiconducting building blocks" *Adv. Mat.*, Vol. 9, p. 36 (1997).

Pentacene, which is a member of polyacene, is one of the most widely studied organic semiconductor and is proposed as semiconducting material for TFT devices in Dimitrakopoulos et al., "Molecular Beam Deposited Thin film of Pentacene for Organic Field-effect Transistor Applications," *J. Appl. Phys.*, 1996, 80, pages 2501–2508, Jackson et al., "Pentacene Organic Thin-film Transistors for Circuit and Display Applications", IEEE Trans. Electron Devices 1999, 46, pages 1259–1263, Dimitrakopoulos et al., "Fabrication of Thin Film Field Effect Transistor Comprsing an Organic Semiconductor and Chemical Solution Deposited Metal Oxide Gate Dielectric," U.S. Pat. No. 5,946,551 and Dimitrakopoulos et al., "Low Temperature Thin Film Transistor Fabrication," U.S. Pat. No. 6,207,472 B1.

Pentacene has shown the highest field effect mobility (greater than 1 cm$^2$ V$^{-1}$ sec$^{-1}$) and high on/off ratio (greater than 10$^7$) among organic semiconductors. The fact that the mobility is comparable, to amorphous silicon ($\alpha$-Si:H) indicates that pentacene may be applied in large-area microelectronic applications such as TFT backplanes for active matrix displays and low end and low cost integrated circuits. However, for an organic semiconductor technology to be a viable low cost alternative to amorphous silicon, it must be soluble in organic solvents to be suitable for application on large areas by inexpensive methods, such as, stamping, screen printing and spin-coating.

Pentacene is virtually insoluble in organic solvents. Presently, pentacene thin films are deposited by costly high vacuum techniques for application in TFT and other electronic devices. Although there has been one example in the literature to form pentacene films through a soluble precursor of pentacene (see Muellen et al., "A soluble pentacene precursor: Synthesis, solid state conversion to pentacene and application in a field-effect transistor," *Adv. Mat.*, Vol. 11, 1999, pages 480–483), the lengthy synthetic approach to the pentacene precursor with very low overall yield makes that approach impractical and commercially unattractive.

Therefore, it is an object of the present invention to prepare thin films of a polycyclic aromatic compound, such as, pentacene, by solid state conversion of thin films of an organic solvent soluble precursor thereof to the polycyclic aromatic compound.

It is another object of the present invention to prepare thin films of an organic solvent soluble precursor of a polycyclic aromatic compound by applying a solution of the precursor in an organic solvent onto a substrate and thereafter removing the solvent.

It is still another object of the present invention to use soluble precursors of a polycyclic aromatic compound, which is a Diels-Alder adduct of the polycyclic aromatic compound with a hetero dienophile, such as, dialkyl azodicarboxylate, acyl nitroso compound, N-sulfinyl amide, thioxocarboxylate and malonate.

It is yet another object of the present invention to use a thin film of a polycyclic aromatic compound, such as, pentacene, in a thin film transistor in which the polycyclic aromatic compound film acts as a p-type semiconductor channel.

It is further another object of the present invention to provide films of a polycyclic aromatic compound, such as, pentacene, for the fabrication of TFT devices that are prepared by a low to moderate temperature conversion of a precursor thereof to the polycyclic aromatic compound at about 80° C. to about 250° C. in a retro-Diels-Alder reaction.

None of the above references describes precursors of polycyclic aromatic compounds that are: (1) Diels-Alder adducts of a polycyclic aromatic compound, such as, pentacene, with a dienophile; (2) highly soluble in common organic solvents; and (3) used to prepare a thin film transistor in which the polycyclic aromatic compound film acts as a p-type semiconductor channel.

The present invention provides highly soluble precursors of polycyclic aromatic compounds, such as, pentacene, which are synthesized in one step via the Diels-Alder reaction of polycyclic aromatic compound with a variety of dienophiles having at least one heteroatom in the dienophile moiety and are used in the fabrication of TFT devices.

SUMMARY OF THE INVENTION

The present invention provides a thin film transistor device comprising:

a plurality of electrically conducting gate electrodes disposed on a substrate;

a gate insulator layer disposed on said electrically conducting gate electrodes;

an organic semiconductor layer disposed on said insulator layer substantially overlapping said gate electrodes; and a plurality of sets of electrically conductive source and drain electrodes disposed on said organic semiconductor layer such that each of said sets is in alignment with each of said gate electrodes;

wherein said organic semiconductor layer is a polycyclic aromatic compound selected from the group consisting of: oligothiophene, perylene, benzo[ghi]perylene, coronene and polyacene formed from thermal conversion of a precursor thereof.

The present invention further provides a process for preparing a thin film transistor device comprising the steps of:

depositing a plurality of electrically conducting gate electrodes on a substrate;

depositing a gate insulator layer on said electrically conducting gate electrodes;

depositing a layer of a polycyclic aromatic compound precursor on said insulator layer such that said layer of polycyclic aromatic compound precursor substantially overlaps said gate electrodes;

depositing a plurality of sets of electrically conductive source and drain electrodes on said layer of polycyclic aromatic compound precursor such that each of said sets is in alignment with each of said gate electrodes; and heating to convert said polycyclic aromatic compound precursor to a polycyclic aromatic compound, thereby producing the thin film transistor device.

Advantages of thin film transistor devices of the present invention include employing an organic semiconductor layer, which can be processed at low temperature. The low temperature processing combined with ease of deposition of thin films over large areas due to the solubility of the precursors of the polycyclic aromatic compounds, i.e., the Diels-Alder adducts, provide an inexpensive approach to the fabrication of a thin film transistor devices according to the present invention. Thus, the low temperature processing characteristics enable the fabrication of organic thin film transistors (OTFT) on plastic substrates that are light weight and possess mechanical flexibility and ruggedness.

BRIEF DESCRIPTION OF DRAWINGS

FIG. 3b shows a plot $I_D$ vs. $V_G$ at a constant, relatively low $V_D$, ($V_D$=40 V), corresponding to the same device as FIG. 3a.

FIG. 5b shows a plot $I_D$ vs. $V_G$ at a constant, relatively low $V_D$, ($V_D$=20 V), corresponding to the same device as FIG. 5a.

DETAILED DESCRIPTION OF THE INVENTION

Figure 1A:
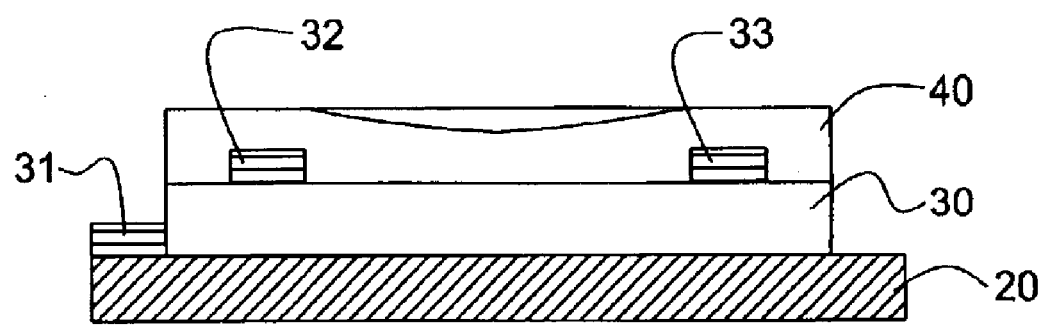
FIG. 1a shows a field-effect transistor (10) with bottom contact geometry with thin film of the precursor (layer 40).

The present invention describes a thin film transistor (TFT) device using an organic semiconductor. In the devices of the present invention, the organic semiconductor layer (also referred to as the active layer) is a polycyclic aromatic compound, preferably a member of polyacenes. An important member of polyacenes is pentacene.

The thin film transistor layer of the present invention is formed from a precursor, which is a Diels-Alder adduct of a polycyclic aromatic compound with a dienophile, wherein the polycyclic aromatic compound is selected from: oligothiophene, perylene, benzo[ghi]perylene, coronene and polyacene; and wherein the dienophile is represented by the formula:

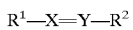

wherein each X and Y can independently be N or $CR^7$;
wherein $R^1$—X= can be O, S, SO and $SO_2$; and
wherein each $R^1$, $R^2$ and $R^7$ can independently be hydrogen, alkyl of 1–12 carbon atoms, aryl, substituted aryl, aralkyl, alkoxycarbonyl, aryloxycarbonyl, acyl and a group R, wherein R can be hydrogen, alkyl of 1–12 carbon atoms, alkoxy, acyl, aryl, aralkyl, chloroalkyl, fluoroalkyl and substituted aryl having a substituent selected from: —F, —Cl, —Br, —$NO_2$, —$CO_2R$, —$PO_3H$, —$SO_3H$, trialkylsilyl and acyl; wherein the acyl is represented by the formula: $R^8CO$— wherein $R^8$ can be hydrogen, alkyl of 1–12 carbon atoms, aryl, substituted aryl, aralkyl and fluoroalkyl;
with the proviso that at least one of X and Y is a hetero atom selected from: N, O and S.

The Diels-Alder adducts of polycyclic aromatic compounds, such as, oligothiophene, perylene, benzo[ghi]

perylene, coronene, oligothiophene and polyacenes, with variety of dienophiles containing at least one heteroatom and in some cases two heteroatoms bonded to aromatic moiety, such as, thioxomalonates, azodicarboxylates, thialdehyde, acylnitroso and N-sulfinylamides are organic solvent-soluble.

The Diels-Alder adducts are prepared by a simple, one step cycloaddition reaction of the polycyclic aromatic compounds, such as, pentacene, or other fused aromatic compounds, with heterodienophiles. The Diels-Alder adducts according to the present invention all form soluble adducts with pentacene and can be converted back to pentacene by retro-Diels-Alder reaction at moderate (60–250° C.) temperatures both in bulk, in solution or as thin-films.

Applicants have discovered that Diels-Alder adducts according to the present invention having one to two heteroatoms bonded to aromatic moiety makes such adducts undergo a retro-Diels-Alder reactions at low to moderate temperatures.

Applicants have also discovered that the Diels-Alder reactions with heterodienophiles are catalyzed by variety of Lewis acid catalysts and are carried out at low to moderate temperatures.

Although there has been great body of work on Diels-Alder reactions and adducts of anthracene (structure I, n=1) which is the second member of polyacenes, very little or no work has been reported on Diels-Alder reactions or adducts for higher members of these class of compound like tetracene (n=2) and particulary for pentacene (n=3).

This might be due to the fact that higher members of polyacenes are not soluble in most organic solvents.

The present invention describes a simple approach in which pentacene (or other polyacenes of I) are treated with a dienophile (formula II) to form a Diels-Alder adduct represented by formula III.

R1—X=Y—R2    I

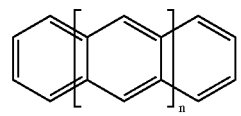

II

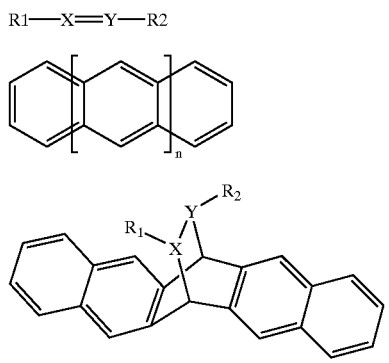

III wherein each X and Y is independently selected from: N and $CR^7$;

wherein $R^1$—X= can be O, S, SO and $SO_2$; and wherein each $R^1$, $R^2$ and $R^7$ is independently selected from: hydrogen, alkyl of 1–12 carbon atoms, aryl, substituted aryl, aralkyl, alkoxycarbonyl, aryloxycarbonyl, acyl and a group R, wherein R can be hydrogen, alkyl of 1–12 carbon atoms, alkoxy, acyl, aryl, aralkyl, chloroalkyl, fluoroalkyl and substituted aryl having a substituent selected from: —F, —Cl, —Br, —$NO_2$, —$CO_2R$, —$PO_3H$, —$SO_3H$, trialkylsilyl and acyl; wherein the acyl is represented by the formula: $R^8CO$— wherein $R^8$ can be hydrogen, alkyl of 1–12 carbon atoms, aryl, substituted aryl, aralkyl and fluoroalkyl;

with the proviso that at least one of X and Y is a hetero atom selected from: N, O and S.

Polyacenes are compounds, which can be represented by the formula:

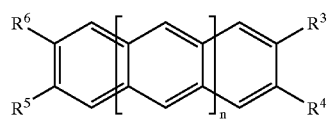

wherein each $R^3$, $R^4$, $R^5$ and $R^6$ is independently selected from: hydrogen, alkyl of 1–12 carbon atoms, aryl, substituted aryl, a group wherein $R^3$ and $R^4$ together form one or more fused benzo rings and a group wherein $R^5$ and $R^6$ together form one or more fused benzo rings, wherein n is at least 1, and preferably, n is at least 2.

The polyacene can be represented by the formula:

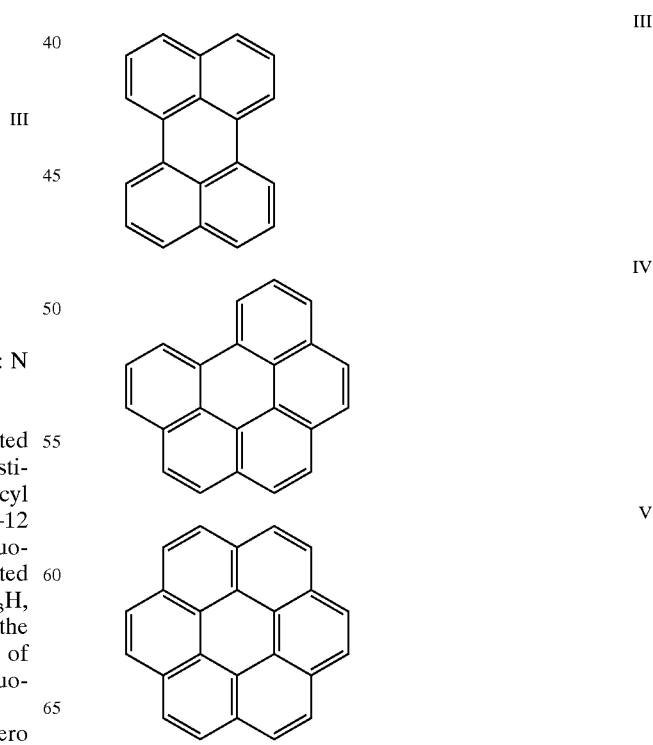

where n is from 2 to 6. In a preferred embodiment, n is equal to 3 such that the polycyclic aromatic compound represented by the above formula represents pentacene. A notable example of the polyacenes is pentacene.

The Diels-Alder reactions can easily be carried out with other members of polyacenes like tetracene and hexacene. Other fused aromatic compounds like oligothiophene, perylene (III), benzo[g,h]perylene (IV), coronene (V) and other fused aromatic compounds capable of forming Diels-Alder adducts can also be used to prepared soluble precursors of these sparingly soluble compounds:

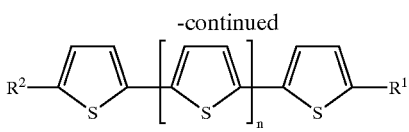

Oligothiophene wherein n is equal or greater than 1, and preferably from 1 to 5; and wherein $R^1$ and $R^2$ are independently selected from the group consisting of hydrogen, alkyl of 1–12 carbon atoms, acyl, alkylphosphonate, hydroxyalkyl, mercaptoalkyl, thiol, carboxylic acid, carboxylic acid ester, trialkoxysilane, amino, alkylamino, dialkylamino and aminoalkane.

The dienophile is represented by the formula:

$R^1$—X=Y—$R^2$ wherein each X and Y is independently selected from: N and $CR^7$;
wherein $R^1$—X= can be O, S, SO and $SO_2$; and
wherein each $R^1$, $R^2$ and $R^7$ is independently selected from: hydrogen, alkyl of 1–12 carbon atoms, aryl, substituted aryl, aralkyl, alkoxycarbonyl, aryloxycarbonyl, acyl and a group R, wherein R can be hydrogen, alkyl of 1–12 carbon atoms, alkoxy, acyl, aryl, aralkyl, chloroalkyl, fluoroalkyl and substituted aryl having a substituent selected from: —F, —Cl, —Br, —$NO_2$, —$CO_2$R, —$PO_3$H, —$SO_3$H, trialkylsilyl and acyl; wherein the acyl is represented by the formula: $R^8$CO— wherein $R^8$ can be hydrogen, alkyl of 1–12 carbon atoms, aryl, substituted aryl, aralkyl and fluoroalkyl;
with the proviso that at least one of X and Y is a hetero atom selected from: N, O and S.

The Diels-Alder adduct is prepared by a process which includes the steps of:
contacting:
(a) a polycyclic aromatic compound selected from: oligothiophene, perylene, benzo[ghi]perylene, coronene and a compound represented by the formula:

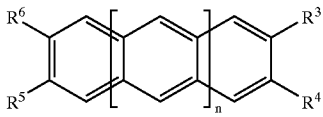

wherein each $R^3$, $R^4$, $R^5$ and $R^6$ is independently selected from: hydrogen, alkyl of 1–12 carbon atoms, aryl, substituted aryl, a group wherein $R^3$ and $R^4$ together form one or more fused benzo rings and a group wherein $R^5$ and $R^6$ together form one or more fused benzo rings, wherein n is at least 1; and
(b) dienophile represented by the formula:

$R^1$—X=Y—$R^2$ wherein each X and Y is independently selected from: N and $CR^7$; wherein $R^1$—X= can be O, S, SO and $SO_2$; wherein each $R^1$, $R^2$ and $R^7$ is independently selected from: hydrogen, alkyl of 1–12 carbon atoms, aryl, substituted aryl, aralkyl, alkoxycarbonyl, aryloxycarbonyl, acyl and a group R, wherein R can be hydrogen, alkyl of 1–12 carbon atoms, alkoxy, acyl, aryl, aralkyl, chloroalkyl, fluoroalkyl and substituted aryl having a substituent selected from: —F, —Cl, —Br, —$NO_2$, —$CO_2$R, —$PO_3$H, —$SO_3$H, trialkylsilyl and acyl; wherein the acyl is represented by the formula: $R^8$CO— wherein $R^8$ can be hydrogen, alkyl of 1–12 carbon atoms, aryl, substituted aryl, aralkyl and fluoroalkyl; with the proviso that at least one of X and Y is a hetero atom selected from: N, O and S;
wherein the contacting is carried out under reaction conditions sufficient to produce the Diels-Alder adduct.

In a preferred embodiment where the polycyclic aromatic compound is a polyacene, the Diels-Alder adduct can be represented by the formula:

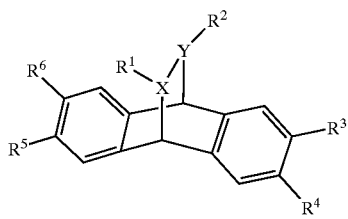

wherein each X and Y is independently selected from: N and $CR^7$;
wherein $R^1$—X= can be O, S, SO and $SO_2$; and
wherein each $R^1$, $R^2$ and $R^7$ is independently selected from: hydrogen, alkyl of 1–12 carbon atoms, aryl, substituted aryl, aralkyl, alkoxycarbonyl, aryloxycarbonyl, acyl and a group R, wherein R can be hydrogen, alkyl of 1–12 carbon atoms, alkoxy, acyl, aryl, aralkyl, chloroalkyl, fluoroalkyl and substituted aryl having a substituent selected from: —F, —Cl, —Br, —$NO_2$, —$CO_2$R, —$PO_3$H, —$SO_3$H, trialkylsilyl and acyl; wherein the acyl is represented by the formula: $R^8$CO— wherein $R^8$ can be hydrogen, alkyl of 1–12 carbon atoms, aryl, substituted aryl, aralkyl and fluoroalkyl;
with the proviso that at least one of X and Y is a hetero atom selected from: N, O and S.

The dienophiles described in this invention are chosen from known compounds and all have at least one heteroatom, such as, N, O or S, connected by a double bond to a second heteroatom or carbon.

Examples of the dienophiles which are used in this invention include dialkylazodicarboxylate, thiooxomalonates, N-sulfinylamides, acylnitroso compounds and other compounds that fulfill the above requirements.

Diels-Alder reaction of conjugated dienes with ethylenic or acetylenic dienophiles remain one of the most useful transformations in organic synthesis. Heterodienophiles of the type RR'C=X have been employed less frequently but have considerable potential when only one carbon-carbon bond is required in the product.

Because of the high reactivity of these hetero dienophiles and the solubility of dienes used in these examples, the Diels-Alder reactions are mostly carried out at low to room temperatures without the use of any catalyst. In cases where dienes are less reactive and have marginal solubility, like anthracene and its derivatives, the Diels-Alder reaction is carried out at moderate temperatures, usually refluxing in low boiling solvents. But because anthracene and its derivatives are soluble in hot solvents, the reaction can be carried out without the presence of a catalyst.

Higher homologous of polyacene like tetracene and pentacene have little or no solubility in most common organic solvents in which a Diels-Alder reactions is carried out. Because of lack of solubility there has been no report of Diels-Alder reaction of pentacene or tetracene with any dienophiles, and particularly with hetero dienophiles.

In this invention, Diels-Alder reactions and adducts of pentacene with various hetero dienophiles are described.

The common feature of all these reactions will be the use of a Lewis acid to promote the reaction at moderate temperature so that the thermally labile adducts can be isolated.

An example of such an adduct wherein the polycyclic aromatic compound is pentacene and the dienophile is a thioxocarboxylate is represented by the formula:

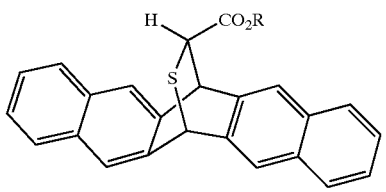

The above Diels-Alder adduct in which the sulfur atom is oxidized to the corresponding sulfoxide is represented by the formula:

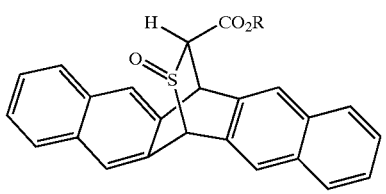

wherein R is selected from: hydrogen, alkyl of 1–12 carbon atoms, alkoxy, acyl, aryl, aralkyl, chloroalkyl, fluoroalkyl and substituted aryl having a substituent selected from: —F, —Cl, —Br, —NO$_2$, —CO$_2$R, —PO$_3$H, —SO$_3$H, trialkylsilyl and acyl; wherein said acyl is represented by the formula: R$^8$CO— wherein R$^8$ is selected from: hydrogen, alkyl of 1–12 carbon atoms, aryl, substituted aryl, aralkyl and fluoroalkyl;

Another example is the Diels-Alder reaction of thioxomalonate with pentacene to form an adduct with one carbon-sulfur bond as depicted in the following scheme. Diethyl thioxomalonate is prepared in situ from the reaction of diethyl oxomalonate and phosphorous pentasulfide and reacted with pentacene in the presence of a catalyst or by heating in pyridine.

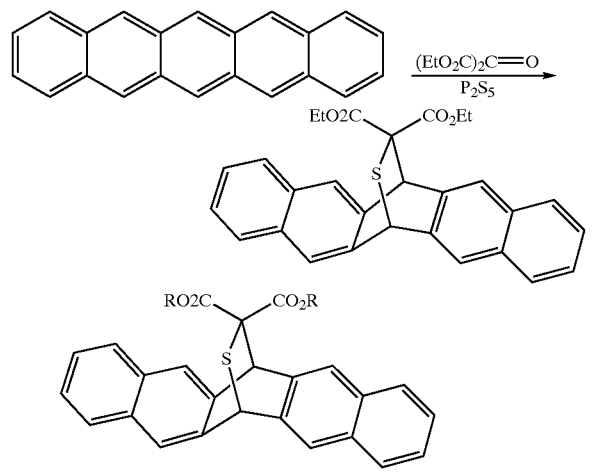

wherein each R is independently selected from: hydrogen, alkyl of 1–12 carbon atoms, alkoxy, acyl, aryl, aralkyl, chloroalkyl, fluoroalkyl and substituted aryl having a substituent selected from: —F, —Cl, —Br, —NO$_2$, —CO$_2$R, —PO$_3$H, —SO$_3$H, trialkylsilyl and acyl; wherein said acyl is represented by the formula: R$^8$CO— wherein R$^8$ is selected from: hydrogen, alkyl of 1–12 carbon atoms, aryl, substituted aryl, aralkyl and fluoroalkyl;

At temperatures higher than 150° C., the thioxomalonate adduct, which is isolated by column chromatography as a white crystalline compound, undergoes a retro Diels-Alder reaction to pentacene. However, if the sulfide is oxidized to corresponding S-oxide, then the adduct can be converted back to pentacene at temperature as low as 150° C.

Both the sulfide and S-oxide adduct are highly soluble in common organic solvents and can be processed from solution to form thin films on substrates.

Another class of adducts of pentacene is Diels-Alder reaction products of pentacene and dialkyl or diaralkylazodicarboxylates. These compounds are by themselves thermally labile and decompose above 100° C. Therefore, any Diels-Alder reaction of these compounds with pentacene has to be carried out low to moderate temperature.

The Diels-Alder adduct where the dienophile is an azodicarboxylate of the formula RO—CO—N=N—COOR is shown below:

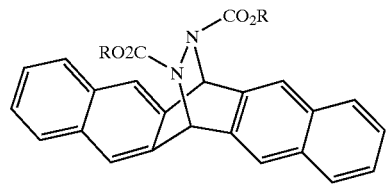

R can be alkyl of 1–12 carbon atoms, aryl, aralkyl, chloroalkyl, fluoroalkyl and substituted aryl having a substituent selected from: —F, —Cl, —Br, —NO$_2$, —CO$_2$R, trialkylsilyl and acyl; wherein the acyl is represented by the formula: R$^8$CO— wherein R$^8$ can be hydrogen, alkyl of 1–12 carbon atoms, aryl, substituted aryl, aralkyl, chloroalkyl and fluoroalkyl.

Preferably, R is benzyl, alkyl of one to five carbon atoms, partially or fully chlorinated alkyl of one to four carbon atoms and partially or fully fluorinated alkyl of one to four carbon atoms.

The above Diels-Alder can be hydrolyzed to form a cyclic diamine compound represented by the formula:

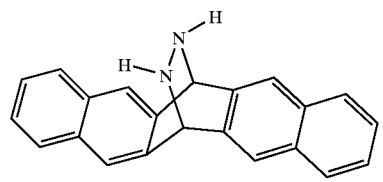

and the diamine can be oxidized to give an azo compound represented by the formula:

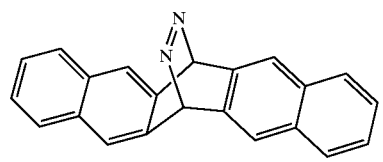

Employing a Lewis acid catalyst, such as, titanium tetrachloride facilitates the Diels Alder reaction so it can be carried out at temperature below −40° C. Alternatively, less active catalysts like silver tetrafluoroborate or methyl rhenium trioxide can be used to run the reaction above room temperature by refluxing the mixture of pentacene, diazodicarboxylate and the catalyst in a low boiling solvent like THF or chloroform.

These diaza adducts of pentacene are stable to high temperatures and as such are not good candidates as pentacene precursors because thin films of these compounds have to be heated above 280° C. to convert to pentacene. For example, the adduct of diethyl diazodicarboxylate (R=ethyl) has a melting point of 257° C. and is stable up to 300° C. But when the carboxylate groups are hydrolyzed to the corresponding acid, which automatically undergo decarboxylation to form the cyclic diamine, or oxidized form of the latter to diazo derivative, then the adduct becomes highly unstable and can be converted back to pentacene at moderate temperatures (50–100° C.). Thus, an important step in this process is the removal of the carboxylate protecting group at low temperatures so as to be able to isolate the amine or diazo compounds.

The adducts of pentacene with a variety of dialkyl azodicarboxylate were prepared. It was found that bis-trichloroethyl carboxylates (R=CCl$_3$—CH$_2$—) can easily be removed at room temperature in THF by treatment with zinc powder to give the corresponding diamine.

In yet another example of Diels-Alder reaction of pentacene with hetero dienophiles, N-Sulfinyl acetamide (R=CH$_3$CO—) and N-sulfinyl benzyl carbamate (R=C$_6$H$_5$CH$_2$OCO—) were prepared and reacted with pentacene in the presence of methyl rhenium trioxide as Lewis acid catalyst. In both cases, high yields of the adduct were obtained and the compounds found to be highly soluble in many organic solvents.

Thin films of these compounds were cast from solution and then heated at 120–140° C. to transform the compounds back to pentacene is confirmed by its UV/VIS spectra (FIG. 1) and thermogravimetric analysis TGA (FIG. 2) and IR spectrum (FIG. 3). Although the onset of the retro Diels-Alder reaction temperature for bulk, as evident from TGA, is about 140° C., thin films of these compounds can be converted back to pentacene at even lower temperatures of 110–120° C.

In still another example of Diels-Alder reaction of pentacene with hetero dienophiles, a Diels-Alder adduct wherein the dienophile is an N-sulfinyl amide compound is represented by the formula:

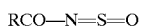

and the adduct is represented by the formula:

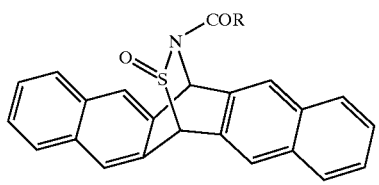

wherein R can be hydrogen, alkyl of 1–12 carbon atoms, alkoxy, acyl, aryl, aralkyl, chloroalkyl, fluoroalkyl and substituted aryl having a substituent selected from: —F, —Cl, —Br, —NO$_2$, —CO$_2$R, —PO$_3$H, —SO$_3$H, trialkylsilyl and acyl; wherein the acyl is represented by the formula: R$^8$CO— wherein R$^8$ can be hydrogen, alkyl of 1–12 carbon atoms, aryl, substituted aryl, aralkyl and fluoroalkyl.

The above Diels-Alder adduct can be hydrolyzed to form a compound represented by the formula:

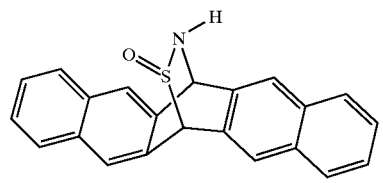

Although only two examples of N-sulfinyl amides are shown here, N-sulfinyl derivatives are equally attractive candidates for the preparation of soluble pentacene adducts.

For example, N-sulfinyl derivative of fluoroalkylamide like trifluoroacetamide (R=CF$_3$—CO—) or higher alkyl amides (R=C$_n$H$_{2n+1}$—CO—, where n=1–10) can be used instead of sulfinyl acetamide. N-Sulfinyl derivatives of aromatic amines (R=aryl) where R— is simply a phenyl group or substituted (nitro, keto, halo, alkyl, fluoroalkyl etc) are known to undergo Diels-Alder reactions and can be used to prepare soluble adducts with pentacene.

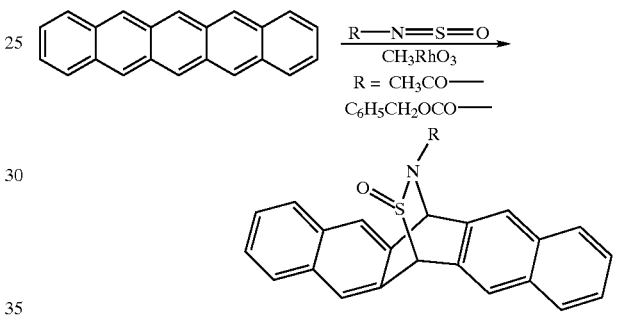

In another example of the Diels-Alder reaction of pentacene with a hetero dienophile, a Diels-Alder adduct wherein the dienophile is a nitroso compound is represented by the formula:

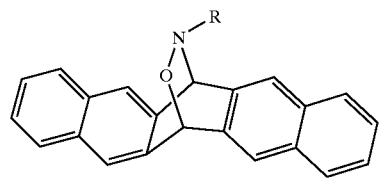

wherein R can be hydrogen, alkyl of 1–12 carbon atoms, alkoxy, acyl, aryl, aralkyl, chloroalkyl, fluoroalkyl, substituted aryl having a substituent selected from: —F, —Cl, —Br, —NO$_2$, —CO$_2$R, —PO$_3$H, —SO$_3$H, trialkylsilyl and acyl; wherein the acyl is represented by the formula: R$^8$CO— wherein R$^8$ can be hydrogen, alkyl of 1–12 carbon atoms, aryl, substituted aryl, aralkyl and fluoroalkyl.

Other acylnitroso compounds of general formula R—CO—N=O are very attractive and judged by its adduct with anthracene derivative can be converted back to pentacene at moderate temperatures. An example would be the reaction of pentacene with N-oxyacetamide (R=CH$_3$—) which can be generated from acetylhydroxamic acid and reacted with pentacene in the presence of methyl rhenium trioxide to give desired adduct as shown bellow.

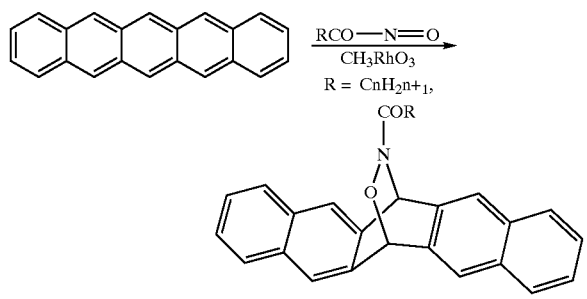

In the above reaction R— can be chosen from alkyl groups of having one to twelve carbon atoms, halogenated alkyl groups like $CF_3$—$(CF_2)_n$— where n is from zero to 10. R could be also an aryl group like phenyl or substituted phenyl with substituents like one or more halogens (Cl, F and Br), nitro group, carboxylic acid or esters, amines or amides, phosphonic acid or ester, trialkyl or trialkoxysilane.

The adducts in which nitrogen is connected to an acyl (RCO) group could further be hydrolyzed to corresponding —NH group by treatment with base as shown in the following reaction.

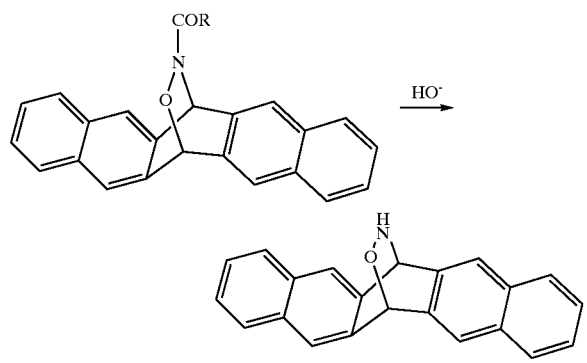

Thin films of these adducts are prepared from solution by different techniques, e.g., spin-coating, casting, doctor blading, etc. Once thin films of these adducts on substrates are formed, they can easily be converted back to pentacene by heating the substrate on a hot plate or in an oven at modest temperatures. Any residual compounds other than pentacene formed during retro Diels-Alder reaction can be removed by dipping the substrate solvents like alcohols, ethers, ketones and the like, to get pure pentacene films.

In the examples listed above the diene which was employed in Diels-Alder reactions has been pentacene, but other members of polyacenes like tetracene, hexacene and heptacene (structure I, n=2, 4 and 5 respectively) can also be used to make soluble derivatives with hetero dienophiles.

Although in all the structures depicted so far, the dienophile has attached to the middle ring of pentacene (or polyacene in general) it is possible to have the dienophile react with other ring in polycyclic aromatic compounds like pentacene, as depicted in the following structure with $R^1$—X=Y—$R^2$ representing hetero dienophiles of this invention:

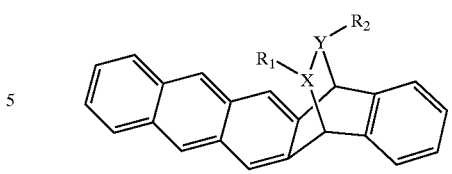

wherein each X and Y is independently selected from: N and $CR^7$;

wherein $R^1$—X= can be O, S, SO and $SO_2$; and wherein each $R^1$, $R^2$ and $R^7$ is independently selected from: hydrogen, alkyl of 1–12 carbon atoms, aryl, substituted aryl, aralkyl, alkoxycarbonyl, aryloxycarbonyl, acyl and a group R, wherein R can be hydrogen, alkyl of 1–12 carbon atoms, alkoxy, acyl, aryl, aralkyl, chloroalkyl, fluoroalkyl and substituted aryl having a substituent selected from: —F, —Cl, —Br, —$NO_2$, —$CO_2R$, —$PO_3H$, —$SO_3H$, trialkylsilyl and acyl; wherein the acyl is represented by the formula: $R^8CO$— wherein $R^8$ can be hydrogen, alkyl of 1–12 carbon atoms, aryl, substituted aryl, aralkyl and fluoroalkyl;

with the proviso that at least one of X and Y is a hetero atom selected from: N, O and S.

The Diels-Alder adducts can be prepared by a process comprising the step of:

contacting a polycyclic aromatic compound and a dienophile represented by the formula $R^1$—X=Y—$R^2$ wherein the contacting is carried out under reaction conditions sufficient to produce the Diels-Alder adduct.

The Diels-Alder reaction of hetero dienophiles with polyacenes and other fused aromatic compounds are Lewis acid-catalyzed. The Diels-Alder reaction is carried out at low to moderate temperatures, as the case may be, resulting in the formation of the adducts. Preferably, the Diels-Alder reaction is carried out in the presence of a Lewis acids and protic acids, including compounds, such as, titanium(IV) tetrachloride, tin(IV)tetrachloride, silver tetrafluoroborate, methyl rhenium trioxide, aluminum chloride, diethyl aluminum chloride, silver trifluoroacetate, palladium compounds, sulfuric acid, trifluoroacetic acid, methanesulfonic acid, trifluoromethanesulfonic acid, and many others Lewis and protic acids known in the art.

The reactions are carried out in the presence of a Lewis acid catalyst to lower the transition state energy of the reaction and to be able to run the reaction at temperatures from below zero to moderate temperatures where the adducts are stable.

Depending on the nature of the dienophile and Lewis acid, Diels-Alder reactions can be carried out at very low temperatures (–70° C. to –40° C.) or room temperature or in refluxing low boiling solvents like THF, acetonitrile or chloroform. Diels-Alder reactions of this invention proceeds to give adducts in high yield and the isolation and purification steps are simple. For this reason, the reaction can easily be scaled up for large-scale preparation of the adducts. The products, which are formed in more than 90% yield, can be separated by evaporation of the solvents at reduced pressure and purified by flash chromatography.

The adducts are soluble in variety of common organic solvents including hydrocarbons, chlorinated hydrocarbons, ethers, esters and ketones. This property of the adducts affords the preparation of thin films of the adduct.

The method of forming a thin film of a Diels-Alder adduct of a polycyclic aromatic compound with a dienophile includes the steps of:

(a) applying onto a substrate a solution of a Diels-Alder adduct of a polycyclic aromatic compound with a dienophile in a suitable solvent: and (b) evaporating the solvent to produce the thin film of the Diels-Alder adduct of the polycyclic aromatic compound with the dienophile.

Thin films of the polycyclic aromatic compound can be formed by a method, which includes the steps of:

(a) applying onto a substrate a solution of a Diels-Alder adduct of a polycyclic aromatic compound with a dienophile in a suitable solvent;

(b) evaporating the solvent to produce the thin film of the Diels-Alder adduct of the polycyclic aromatic compound with the dienophile; and (c) heating the thin film of the Diels-Alder adduct at a temperature and for a period of time sufficient to convert the Diels-Alder adduct back to the polycyclic aromatic compound.

Thin films of these adducts are cast from solution and they can be converted back to pentacene films by simply heating the substrate on which it is coated.

Any suitable substrate can be used to prepare the thin films of the polycyclic aromatic compounds of the present invention as well as the thin films of the Diels-Alder adducts thereof. Preferably, the substrate used to prepare the above thin films is a metal, silicon, plastic, glass or coated glass.

The temperature of the retro-Diels-Alder reaction (conversion of the adducts to pentacene) is dependent on the nature of the dienophile used to prepare the adduct. The conversion can be carried out at temperatures as low as 60° C. in the case of the pentacene diazodicarboxylate adduct after hydrolysis, to more than 180° C. in the case of adduct with thioxomalonate. However, typically, the temperature of heating the thin film of the Diels-Alder adduct is from about 80° C. to about 250° C.

Thin film transistors (TFT) of the present invention use polycyclic aromatic compounds, such as, pentacene, as an organic semiconductor channel.

In general, the polycyclic aromatic compound films are deposited by solution application of a polycyclic aromatic compound precursor on a highly doped silicon substrate covered with a thin film of thermally grown oxide as gate dielectric. The substrate is then heated to convert the thin film of the polycyclic aromatic compound precursor to a thin film of the polycyclic aromatic compound. Source and drain electrodes are then deposited on top of the polycyclic aromatic compound film thus formed to get a TFT device.

Preferably, the polycyclic aromatic compound is pentacene. In the case of pentacene, heating converts the pentacene precursor layer to a pentacene layer. The pentacene films used in the devices of the present invention are prepared by heating a film of a pentacene precursor at temperatures from about 80° C. to about 250° C.

Alternatively, a TFT is fabricated by, for example, by solution deposition of a pentacene precursor on a highly doped silicon substrate covered with a thermally grown oxide layer followed by vacuum deposition and patterning of source and drain electrodes. In the last step, the device is heated so that the pentacene precursor is converted to a pentacene film.

In yet another approach, a TFT is fabricated by deposition of source and drain electrodes on a highly doped silicon substrate covered with a thermally grown oxide and then solution deposition of a pentacene precursor to form a thin film of the latter and finally heating the device to convert the pentacene precursor to pentacene.

The gate electrode could also be a patterned metal gate electrode on a substrate or a conducting material such as, a conducting polymer, which is then coated with an insulator applied either by solution coating or by vacuum deposition on the patterned gate electrodes. The insulator can be a material, such as, an oxide, nitride, or it can be a material selected from the family of ferroelectric insulators, including but not limited to $PbZr_xTi_{1-x}O_3$ (PZT), $Bi_4Ti_3O_{12}$, $BaMgF_4$, $Ba(Zr_{1-x}Ti_x)O_3$ (BZT), or it can be an organic polymeric compound.

The pentacene precursors are dissolved in a suitable organic solvent including but not limited to chloroform, tetracloroethane, tetrahydrofuran, toluene, ethyl acetate, methyl ethyl ketone, dimethyl formamide, dichlorobenzene, propylene glycol monomethyl ether acetate (PGMEA) and mixtures thereof. The solution is then applied by a method, such as, spin-coating, dip-coating, screen printing, microcontact printing, doctor blading or other solution application techniques known in the art on the substrate and then heated from about 80° C. to about 250° C. to obtain thin films of pentacene. Any residue from the hetero dienophile remaining in the pentacene film can then be removed either by washing with a solvent or by vacuum drying.

Figure 1B:
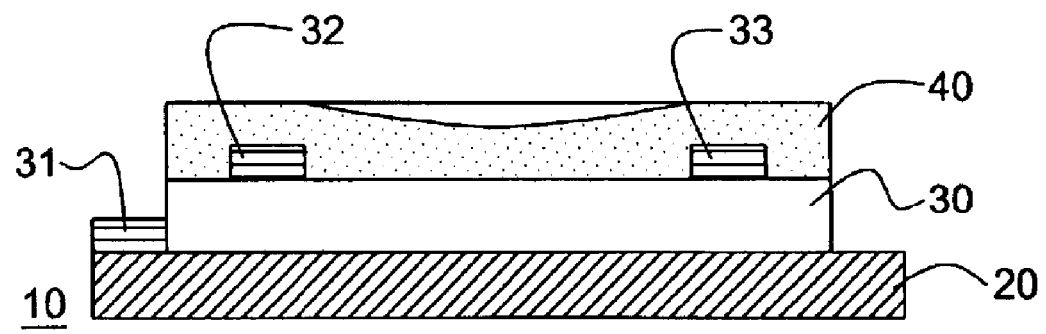
FIG. 1b shows device 10 after the substrate has been heated to convert the precursor to pentacene thin film (layer 41).
Figure 2A:
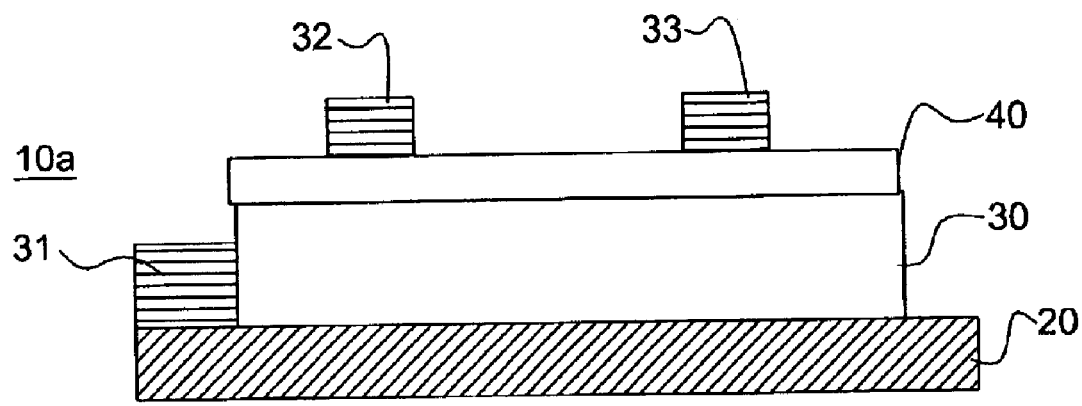
FIG. 2a shows the top contact geometry structure in which the source (32) and drain (33) electrodes are deposited and patterned on top of the precursor layer (40).
Figure 2B:
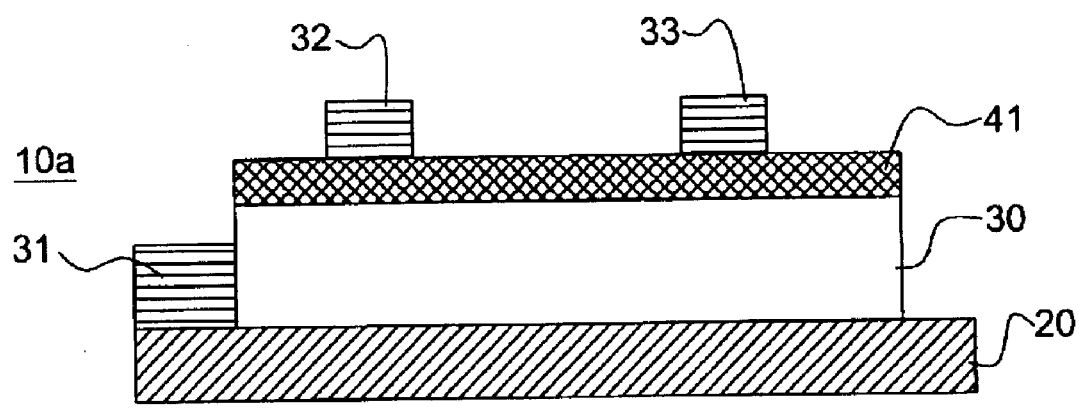
FIG. 2b shows a top contact geometry device of FIG. 2a, in which the precursor layer (40) has been converted to pentacene (41) by heating.

Thin film transistors have the general structure depicted in FIGS. 1b and 2b. These devices 10 are formed on a substrate 20, which is typically glass, silicon, or plastic. If inexpensive and flexible devices are desired, a plastic substrate is usually used as a substrate.

A layer of dielectric 30 is coated on the substrate 20. Suitable dielectric materials are well known to one skilled in the art, including but not limited to materials, such as, silicon dioxide, silicon nitride, aluminum oxide, $PbZr_xTi_{1-x}O_3$ (PZT), $Bi_4Ti_3O_{12}$, $BaMgF_4$, $Ba(Zr_{1-x}Ti_x)O_3$ (BZT) and organic polymeric compounds like MYLAR™ Polyethylene Terephthalate, polycarbonate and polyimide.

Device 10 of the present invention can be fabricated in two different geometries: top contact and bottom contact geometries as shown in FIG. 1b and FIG. 2b, respectively.

In the bottom contact geometry (FIG. 1), a thin film of dielectric 30 is applied on substrate 20 and then three contacts 31, 32 and 33 are deposited by well-known techniques known to a person skilled in the art. A layer of a pentacene precursor (layer 40, FIG. 1a) is then applied from solution by spin-coating or printing or other suitable techniques known in the art.

Any suitable solvent can be used to dissolve the precursor of the polycyclic aromatic compound, provided it can dissolve at least some of the polycyclic aromatic compound. Suitable solvents that can be used to dissolve the pentacene precursors of the present invention include, but are not limited to, chloroform, tetracloroethane, tetrahydrofuran, toluene, ethyl acetate, methyl ethyl ketone, dimethyl formamide, dichlorobenzene, propylene glycol monomethyl ether acetate (PGMEA) and mixtures thereof.

Preferably, the thickness of the polycyclic aromatic compound layer is in the range of from about 5 to about 200 nm and preferably the thickness is in the range of from about 10 to about 30 nm.

Device 10 of FIG. 1a is thereafter heated from about 80° C. to about 250° C. to convert the thin film 40 of the pentacene precursor to pentacene film 41 as shown in FIG. 1b.

Figure 1C:
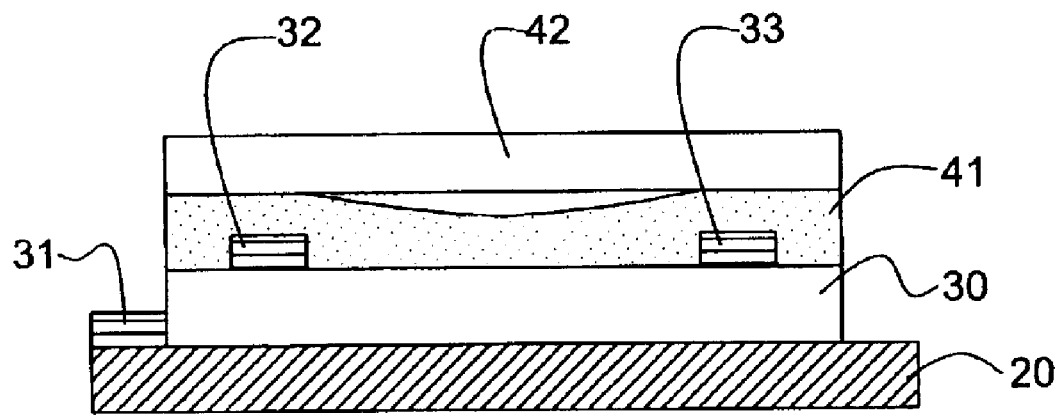
FIG. 1c shows device 10 in which a device as in FIG. 1b has been coated with a second layer of the precursor (layer 42).
Figure 1D:
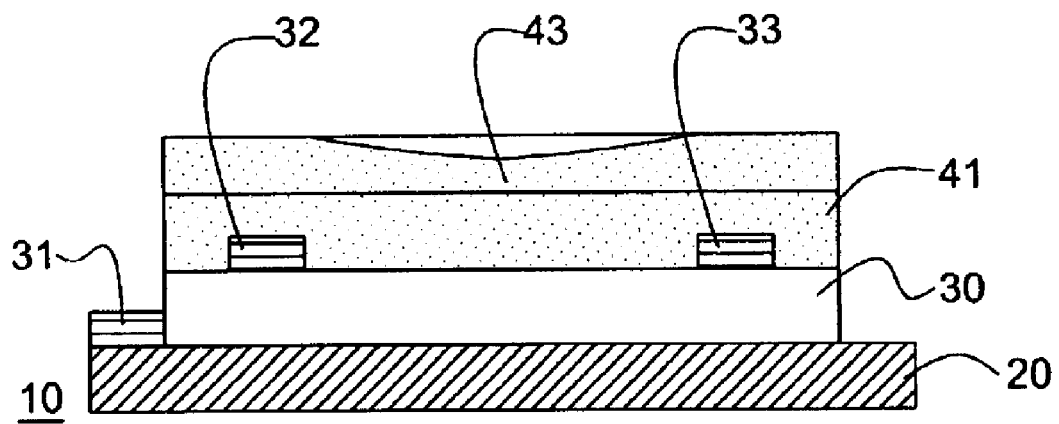
FIG. 1d shows device 10 in which the second precursor layer has been converted to pentacene upon heating (layer 43).
Figure 1E:
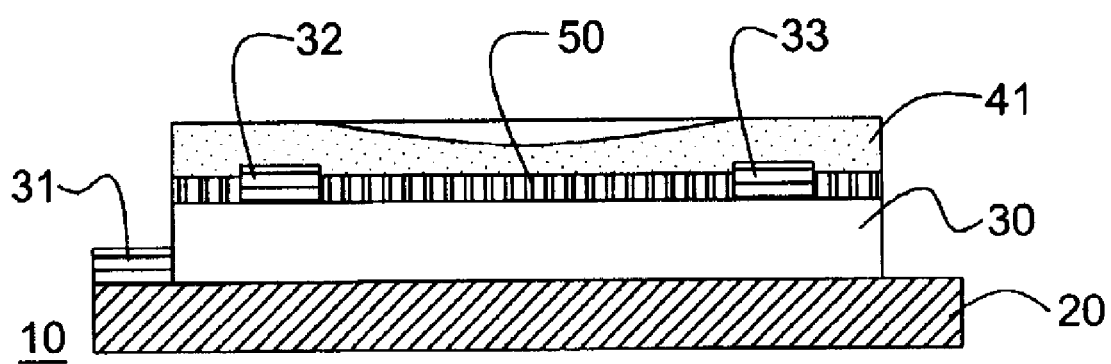
FIG. 1e shows device 10 in which the surface of the gate insulator was modified by application of a layer of the compound hexamethyldisilizane (HMDS) (layer 50), followed by deposition of a thin film of the precursor which was then heated to convert it to pentacene (layer 41).

In one embodiment of the present invention, a second layer 42 of precursor is applied on top of pentacene layer 41 and the device is then heated for a second time to convert the top layer to pentacene layer 43 as shown in FIGS. 1c and 1d, respectively.

Optionally, the device can be rinsed with solvents to remove any unreacted starting materials or products other than pentacene.

In the top contact geometry, after application of the dielectric layer 30 on the substrate 20, pentacene precursor layer 40 is deposited, and the device is heated at a temperatur from about 80° C. to about 250° C. to convert the precursor layer 40 to pentacene layer 41.

An optional second layer of precursor could also be applied from solution and heated for conversion to pentacene so that any holes or discontinuities in the thin film of pentacene 41 are covered.

Further optionally, the coated substrate can be rinsed with a solvent to remove any unreacted starting material or products other than pentacene.

Contacts 32 and 33 (FIG. 2b) are then deposited through a shadow mask to make the completed TFT device shown in FIG. 2b.

In another embodiment of the present invention, the pentacene precursor film of 40 in FIGS. 1 and 2 is deposited by sublimation to get a uniform film of the adduct. The device is then heated to convert the adduct to pentacene film 41.

In a further embodiment of the present invention, a monolayer including a material, such as, hexamethyldisilazine (HMDS), aminopropyl triethoxysilane or alkyl trichlorosilane can be applied onto the gate insulator layer before deposition of the precursor.

In a still further embodiment of the present invention, a self assembled monolayer including a material, such as, alkyl thiol, alkyl phosphonic acid or alkyl hydroxamic acid can be applied onto the surface of the source and the drain electrodes.

Devices of the present invention have field effect mobilities of greater than $10^{-3}$ cm$^2$ V$^{-1}$ sec$^{-1}$ and on/off ratios of greater than 1000.

EXPERIMENTAL

Example 1

Diels-Alder adduct of pentacene and dimethylazodicarboxylate. Pentacene (834 mg, 3 mmole) and methyl rhenium trioxide (50 mg) were added to a solution of dimethylazodicarboxylate (1.05 g, 6 mmole) in 40 mL of anhydrous chloroform and the solution was refluxed for 18 hours. By this time all the pentacene was dissolved and a yellow clear solution was formed.

The solvent was evaporated on rotary evaporator and the residue was flash chromatographed on a column of silica gel first eluting with 9:1 hexane ethyl acetate to remove excess dimethylazodicarboxylate and then elution with 50:50 hexane ethyl acetate gave, after removal of the solvent, the adduct as white powder (1.65 gram, 90% yield), m.p.= 273–275° C., onset of decomposition (conversion back to pentacene) at 285° C. IR, KBr: 1754 and 1701 cm$^{-1}$ (carbonyl groups).

Exact procedure was followed and adducts of pentacene with diethyl azodicarboxylate (m.p=292–294° C.), dibenzylazodicarboxylate (m.p=295–297° C.) and bis-trichloroethylazodicaboxylate were also synthesized in more than 90% yield.

Example 2

Diels-Alder adduct of N-Sulfinyl acetamide and pentacene: Pentacene (556 mg, 2 mmole) was added to a solution of N-sulfinyl acetamide (prepared according to procedure reported by Kin et al., in "New facile synthesis of N-sulfinylamine derivatives using N,N'-sulfinylbisimidazole and N-(chlorosulfinyl)imidazole, Tetrahedron Lett., Vol. 26, 1985, pages 3821-3824) (420 mg, 4 mmole) containing 30 mg. of methyl rhenium trioxide. The mixture was refluxed for 4 hours. The solution was cooled to room temperatures and the solvent was evaporated on rotary evaporator. Excess N-sulfinyl acetamide was removed in high vacuum and the brown solid residue was flash chromatographed on a column of silica gel eluting with 1% methanol in chloroform to give the adduct (690 mg, 91%) as white powder which was crystallized from 2:1 toluene-ethanol. m.p=140–142 (dec.). IR (KBr), 1675, 1376, 1282, 1124 and 893 cm$^{-1}$. Thermogravimetric analysis (FIG. 2), weight loss of 27% starting at 140° C.

Example 3

A thin film transistor having the structure illustrated in FIG. 1a (bottom contact geometry) was fabricated using a solution cast film of a pentacene precursor. A highly doped silicon wafer with 100 to 500 nm of thermally grown oxide was chosen as the substrate and at the same time working as the gate electrode. Gold contacts 32 and 33 were deposited through a shadow mask, and channel width of about 1500 $\mu$m and a channel length of 25.4 $\mu$M were constructed. The substrate was cleaned with standard "piranha" cleaning solution. Then a solution of the Diels-Alder adduct of pentacene with N-Sulfinyl acetamide prepepared according to Example 2 (15 mg/mL) in chloroform was spin-coated at 1000 rpm in nitrogen atmosphere. The film was dried at 80° C. for 30 seconds and then heated in nitrogen atmosphere at 180° C. for 3 minutes to convert the precursor film to pentacene. Completed TFT samples were then tested electrically using a Hewlett Packard Model 4145B semiconductor parameter analyzer to determine their operating characteristics.

The electrical characteristics of TFT's having pentacene as the semiconductor, a heavily doped Si-wafer as the gate electrode, thermally grown SiO$_2$ on the surface of the Si-wafer as the gate insulator, and Au source and drain electrodes, are adequately modeled by standard field effect transistor equations (S. M. Sze "*Physics of Semiconductor Devices*", Wiley, New York, 1981, pg. 442), as shown previously (G. Horowitz, D. Fichou, X. Peng, Z. Xu, F. Garnier, Solid State Commun. Volume 72, pg. 381, 1989; C. D. Dimitrakopoulos, A. R. Brown, A. Pomp, *J. Appl. Phys.* Volume 80, pg. 2501, 1996).

The resulting pentacene films used as active channels in the present devices behave as a p-type semiconductors.

Figure 3A:
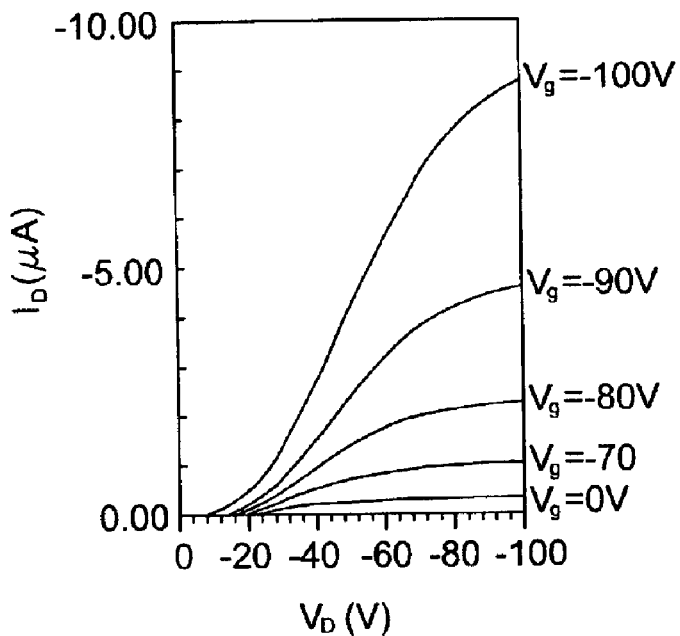
FIG. 3a, shows the dependence of the current flowing between the source and drain electrodes ($I_D$) on the voltage applied to the drain electrode ($V_D$), at discrete voltages applied to the gate electrode ($V_G$) for a device prepared according to Examle 3.

FIG. 3a, shows the dependence of the current flowing between the source and drain electrodes (I$_D$) on the voltage applied to the drain electrode (V$_D$), at discrete voltages applied to the gate electrode (V$_G$). When the gate electrode is biased negatively with respect to the grounded source electrode, pentacene-based TFT's operate in the accumulation mode and the accumulated carriers are holes. At low V$_D$, I$_D$ should increase linearly with V$_D$ (linear region) and is approximately given by the equation:

$$I_D = \frac{WC_i\mu}{L}\left(V_G - V_T - \frac{V_D}{2}\right)V_D$$

wherein L is the channel length, W is the channel width, C$_i$ is the capacitance per unit area of the insulating layer, V$_T$ is a threshold voltage, and $\mu$ is the field effect mobility. The field effect mobility $\mu$ can be calculated in the linear region from the transconductance:

$$g_m = \frac{\partial I_D}{\partial V_G}\bigg|_{V_D=const.} = \frac{WC_i}{L}\mu V_D$$

by plotting $I_D$ vs. $V_G$ (FIG. 3b) at a constant low $V_D$, ($V_D$=40 V), and equating the value of the slope of this plot to $g_m$. In the devices of the present invention, either the source and drain contacts are not ohmic, or there is a large concentration of traps present, or both conditions take place at the same time, which result in the non-linear characteristics at low $V_D$. Despite this, the mobility calculated at $V_D$=−40 V, where the plot exhibits a linear segment, was 0.007 cm$^2$ V$^{-1}$ s$^{-1}$.

When the drain electrode is more negatively biased than the gate electrode (i.e −$V_D$>−($V_G$−$V_T$)), with the source electrode being grounded (i.e. $V_S$=0), the current flowing between source and drain electrodes ($I_D$) tends to saturate, i.e., does not increase further, due to the pinch-off in the accumulation layer (saturation region), and is modeled by the equation:

$$I_D = \frac{WC_i\mu}{2L}(V_G - V_T)^2$$

Figure 4:
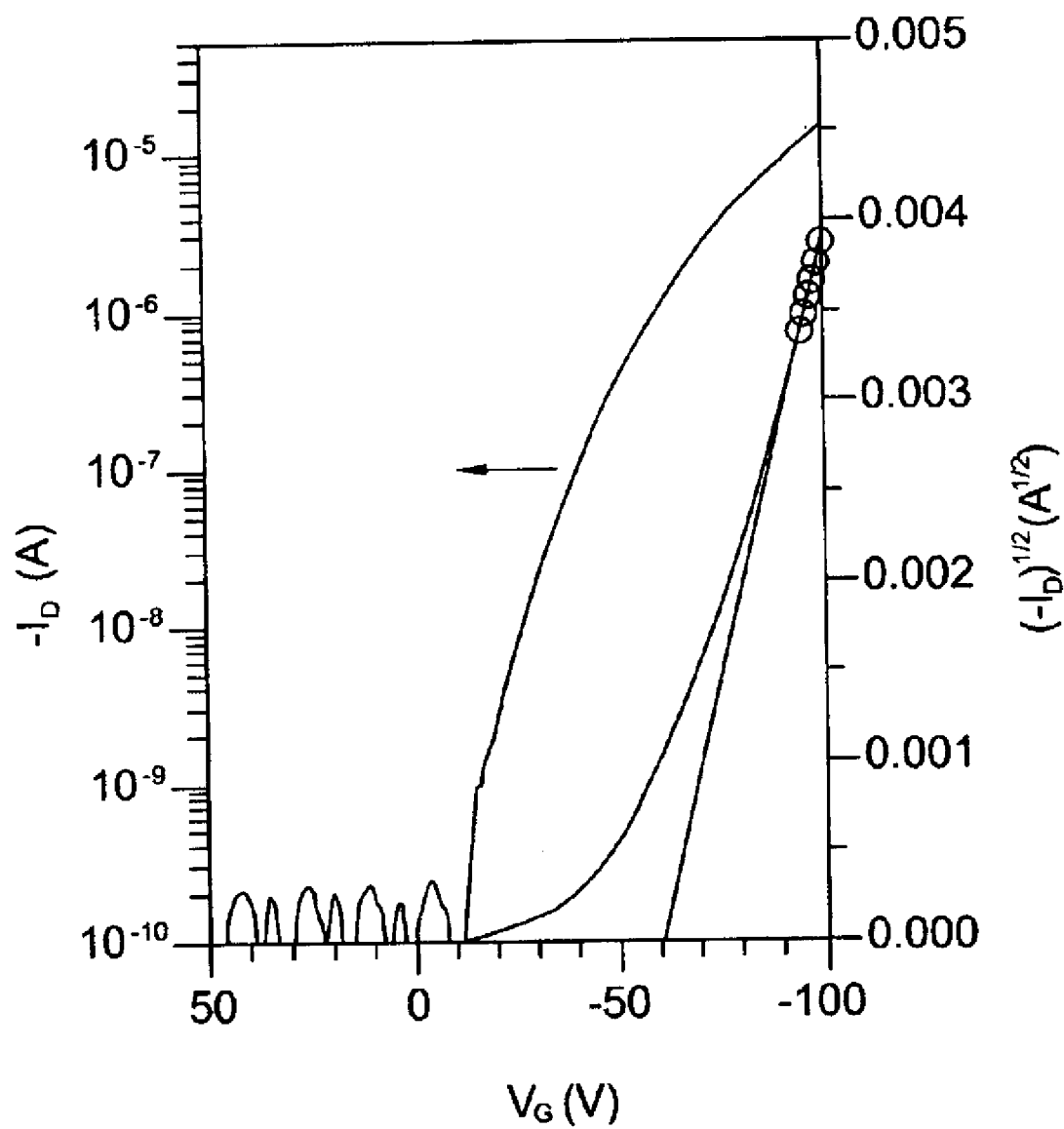
FIG. 4 corresponds to the same device as in FIG. 3b and shows a semilogarithmic plot of the dependence of $I_D$ on $V_G$ in saturation (left y-axis and a plot of the square root of $I_D$ vs $V_G$) (right y-axis), with $V_D$=constant=−100.

FIG. 4 shows a semilogarithmic plot of the dependence of $I_D$ on $V_G$ in saturation (left y-axis). The field effect mobility can be calculated from the slope of the $\sqrt{|I_D|}$ vs. $V_G$ plot in which $V_D$=constant=−100 V.

FIG. 4 (right y-axis) shows a plot of the square root of $I_D$ vs $V_G$. A mobility of 0.05 cm$^2$ V$^{-1}$ sec$^{-1}$ can be calculated from this plot. The threshold voltage $V_T$=−60 V and the current modulation between the on and the off state of the device was about 10$^{5}$.

Example 4

Thin film transistors having the structure illustrated in FIG. 1a (bottom contact geometry) were fabricated using a solution cast film of a pentacene precursor. A highly doped silicon wafer with 500 nm of thermally grown oxide was chosen as the substrate and at the same time working as the gate electrode. Gold contacts 32 and 33 were deposited through a shadow mask defining devices with channel width of about 1500 µm and channel lengths of 15.4 µm and 5 µm. The substrate was cleaned with standard "piranha" cleaning solution. The surface of the gate insulator was modified by application of a layer of the compound hexamethyldisilizane (HMDS) (layer 50, FIG. 1e) before pentacene precursor deposition. Then a solution of the Diels-Alder adduct of pentacene with N-Sulfinyl acetamide prepepared according to Example 2 (15 mg/mL) in chloroform was spin-coated at 1500 rpm in nitrogen atmosphere. The film was dried at room temperature and then heated in nitrogen atmosphere at 200° C. for 1.5 minutes to convert the precursor film to pentacene.

Figure 3B:
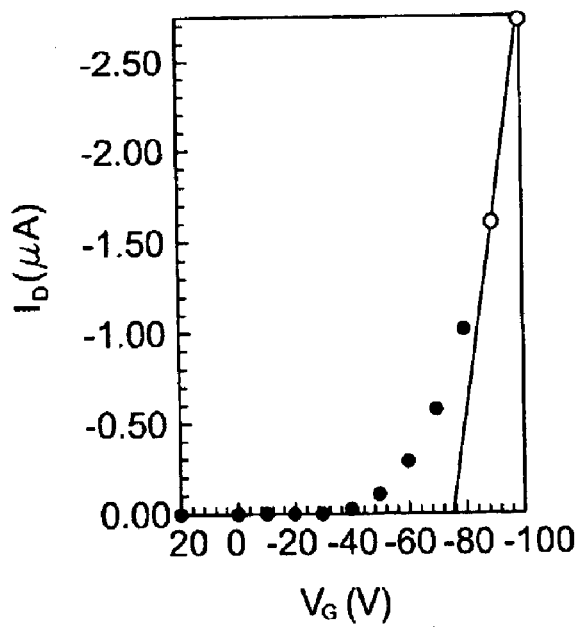
Figure 5A:
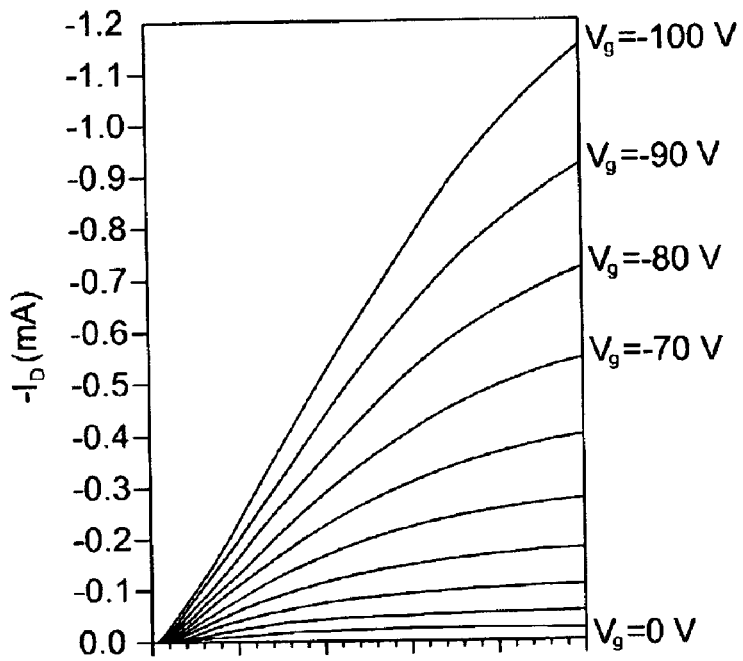
FIG. 5a, shows the dependence of $I_D$ on $V_D$ at discrete voltages applied to the gate electrode $V_G$ for a device prepared according to Example 4.
Figure 5B:
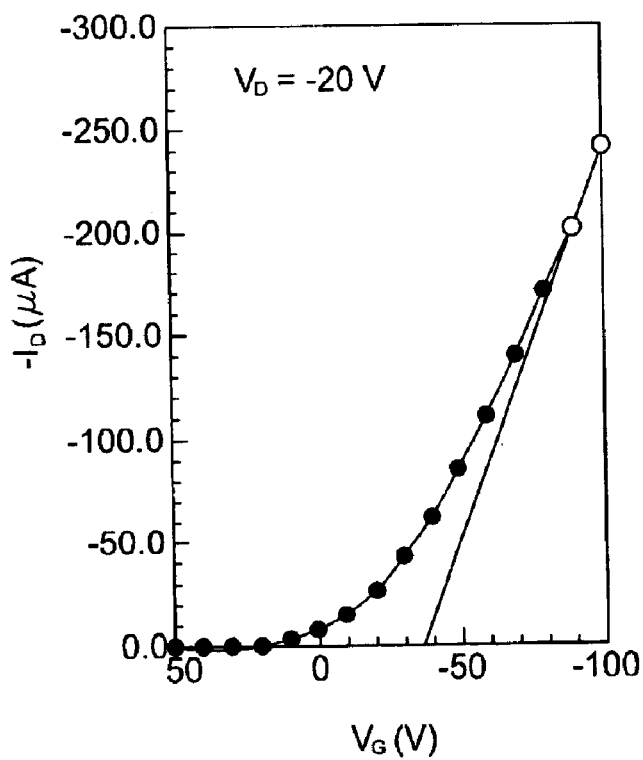

FIGS. 5a and 5b are similar to FIGS. 3a and 3b except that the devices are prepared according to the procedure described in Example 4. The mobility calculated at $V_D$=−20 V (linear regime) was 0.29 cm$^2$ V$^{-1}$s$^{-1}$.

Figure 6:
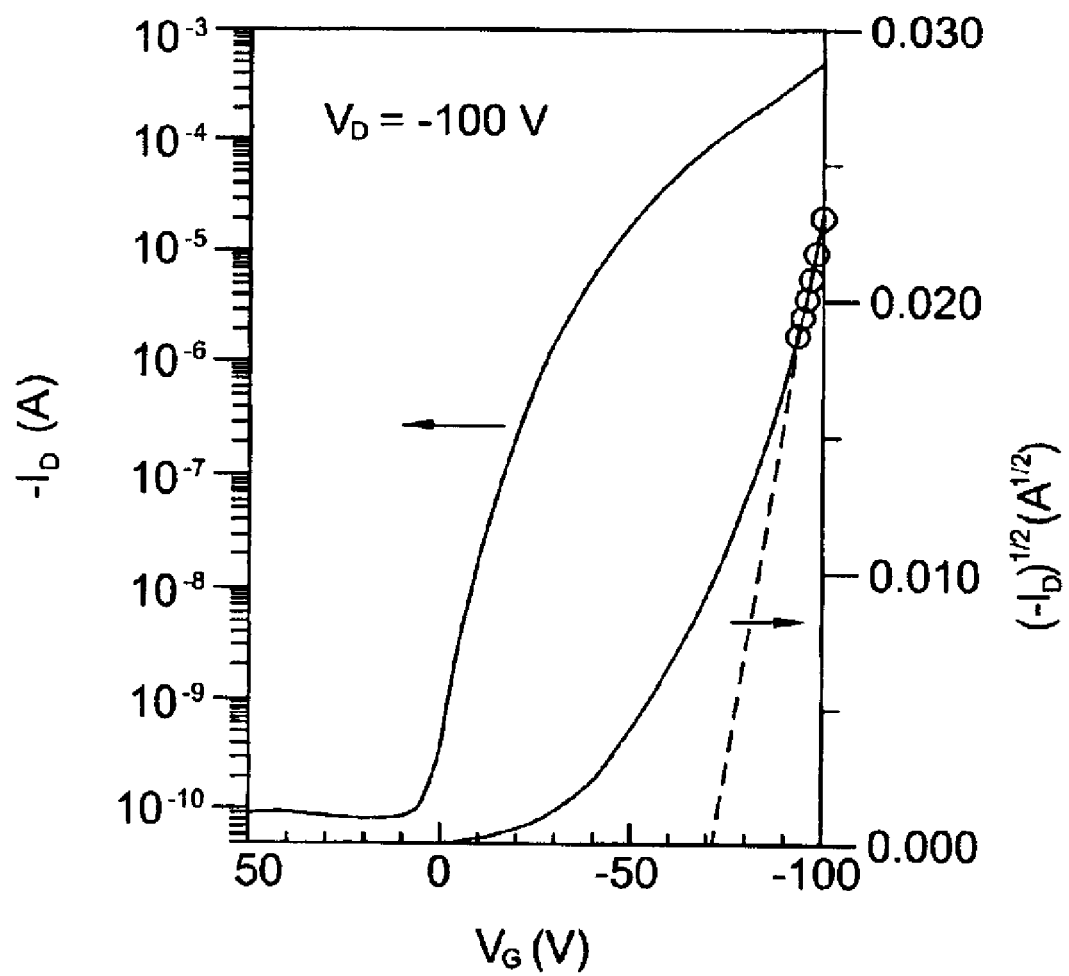
FIG. 6 shows a semilogarithmic plot of the dependence of $I_D$ on $V_G$ in saturation (left y-axis and a plot of the square root of $I_D$ vs $V_G$) (right y-axis), with $V_D$=constant=−100 for a device fabricated according to the process in Example 4.

FIG. 6 (left y-axis) shows a semilogarithmic plot of the dependence of $I_D$ on $V_G$ in saturation from another device that was processed similarly to the device of FIG. 5. FIG. 6 (right y-axis) shows a plot of the square root of $I_D$ vs. $V_G$. A mobility of 0.89 cm$^2$ V$^{-1}$ s$^{-1}$ can be calculated from this plot. The threshold voltage $V_T$=−70 V and the current modulation between the on and the off state of the device was more than 10$^6$.

Alternative work-up and isolation procedures are also possible, and will be evident to those skilled in the art.

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

We claim:

1. A thin film transistor device comprising;

a plurality of electrically conducting gate electrodes disposed on a substrate;

a gate insulator layer disposed on said electrically conducting gate electrodes;

an organic semiconductor layer disposed on said insulator layer substantially overlapping said gate electrodes; and a plurality of sets of electrically conductive source and drain electrodes disposed on said organic semiconductor layer such that each of said sets is in alignment with each of said gate electrodes;

wherein said organic semiconductor layer is a polycyclic aromatic compound selected from the group consisting of: oligothiophene, perylene, benzo[ghi]perylene, coronene and polyacene, wherein said polycyclic aromatic compound is formed from thermal conversion of a Diels-Alder adduct precursor thereof;

wherein said organic semiconductor layer has only a single crystal phase; and wherein a monolayer comprising a material selected from the group consisting of: hexamethyldisilazine (HMDS), aminopropyl triethoxysilane and alkyl trichlorosilane is applied onto said gate insulator layer before deposition of said precursor.

2. The thin film transistor device of claim 1, wherein said precursor is a Diels-Alder adduct of said polycyclic aromatic compound with a dienophile, wherein said dienophile is represented by the formula:

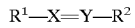

wherein each X and Y is independently selected from the group consisting of: N and CR$^7$;

wherein R$^1$—X= is selected from the group consisting of: O, S, SO and SO$_2$; and wherein each R$^1$, R$^2$ and R$^7$ is independently selected from the group consisting of: hydrogen, alkyl of 1–12 carbon atoms, aryl, substituted aryl, aralkyl, alkoxycarbonyl, aryloxycarbonyl, acyl and a group R, wherein R is selected from the group consisting of: hydrogen, alkyl of 1–12 carbon atoms, alkoxy, acyl, aryl, aralkyl, chloroalkyl, fluoroalkyl and substituted aryl having a substituent selected from the group consisting of: —F, —Cl, —Br, —NO$_2$, —CO$_2$R, —PO$_3$H, —SO$_3$H, trialkylsilyl and acyl; wherein said acyl is represented by the formula: R$^8$CO— wherein R$^8$ is selected from the group consisting of: hydrogen, alkyl of 1–12 carbon atoms, aryl, substituted aryl, aralkyl and fluoroalkyl;

with the proviso that at least one of X and Y is a hetero atom selected from the group consisting of: N, O and S.

3. The thin film transistor device of claim 2, wherein said polycyclic aromatic compound is a polyacene represented by the formula:

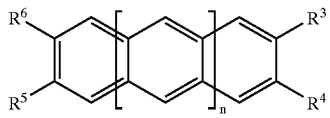

wherein each $R^3$, $R^4$, $R^5$ and $R^6$ is independently selected from the group consisting of: hydrogen, alkyl of 1–12 carbon atoms, aryl, substituted aryl, a group wherein $R^3$ and $R^4$ together form one or more fused benzo rings and a group wherein $R^5$ and $R^6$ together form one or more fused benzo rings;
wherein n is at least 1; and
wherein said Diels-Alder adduct of said polycyclic aromatic compound with said dienophile is represented by the formula:

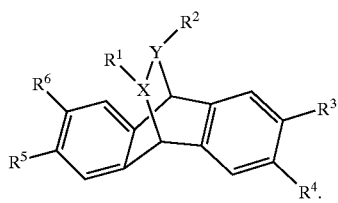

4. The thin film transistor device of claim 3, wherein n is at least 2.
5. The thin film transistor device of claim 4, wherein said polyacene is represented by the formula:

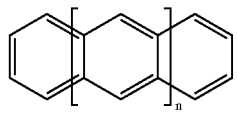

where n is at least 2.
6. The thin film transistor device of claim 5, wherein n is equal to 3 and said polycyclic aromatic compound is pentacene.
7. The thin film transistor device of claim 2, wherein said dienophile is a thioxocarboxylate compound and said adduct is represented by the formula:

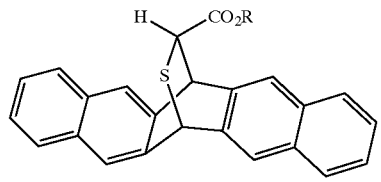

wherein R is selected from the group consisting of: hydrogen, alkyl of 1–12 carbon atoms, alkoxy, acyl, aryl, aralkyl, chloroalkyl, fluoroalkyl and substituted aryl having a substituent selected from the group consisting of: —F, —Cl, —Br, —NO$_2$, —CO$_2$R, —PO$_3$H, —SO$_3$H, trialkylsilyl and acyl; wherein said acyl is represented by the formula: $R^8$CO— wherein $R^8$ is selected from the group consisting of: hydrogen, alkyl of 1–12 carbon atoms, aryl, substituted aryl, aralkyl and fluoroalkyl.

8. The thin film transistor device of claim 7, wherein the sulfur atom is oxidized to corresponding sulfoxide and wherein said adduct is represented by the formula:

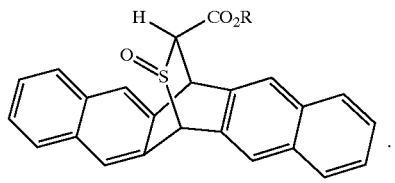

9. The thin film transistor device of claim 2, wherein said dienophile is thioxomalonate and said adduct is represented by the formula:

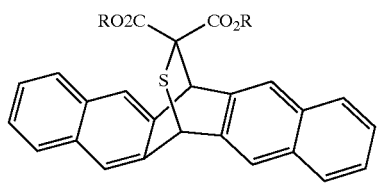

wherein R is selected from the group consisting of: hydrogen, alkyl of 1–12 carbon atoms, alkoxy, acyl, aryl, aralkyl, chloroalkyl, fluoroalkyl and substituted aryl having a substituent selected from the group consisting of: —F, —Cl, —Br, —NO$_2$, —CO$_2$R, —PO$_3$H, —SO$_3$H, trialkylsilyl and acyl; wherein said acyl is represented by the formula: $R^8$CO— wherein $R^8$ is selected from the group consisting of: hydrogen, alkyl of 1–12 carbon atoms, aryl, substituted aryl, aralkyl and fluoroalkyl.

10. The thin film transistor device of claim 2, wherein said dienophile is a nitroso compound and said adduct is represented by the formula:

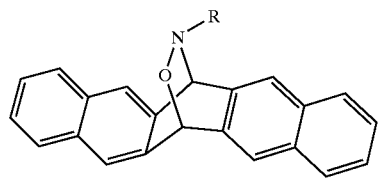

wherein R is selected from the group consisting of: hydrogen, alkyl of 1–12 carbon atoms, alkoxy, acyl, aryl, aralkyl, chloroalkyl, fluoroalkyl, substituted aryl having a substituent selected from the group consisting of: —F, —Cl, —Br, —NO$_2$, —CO$_2$R, —PO$_3$H, —SO$_3$H, trialkylsilyl and acyl; wherein said acyl is represented by the formula: $R^8$CO— wherein $R^8$ is selected from the group consisting of: hydrogen, alkyl of 1–12 carbon atoms, aryl, substituted aryl, aralkyl and fluoroalkyl.

11. The thin film transistor device of claim 2, wherein said dienophile is an N-sulfinyl amide compound represented by the formula:

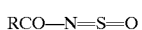

wherein said adduct is represented by the formula:

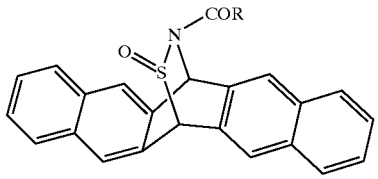

and
wherein R is selected from the group consisting of: hydrogen, alkyl of 1–12 carbon atoms, alkoxy, acyl, aryl, aralkyl, chloroalkyl, fluoroalkyl and substituted aryl having a substituent selected from the group consisting of: —F, —Cl, —Br, —NO$_2$, —CO$_2$R, —PO$_3$H, —SO$_3$H, trialkylsilyl and acyl; wherein said acyl is represented by the formula: R$^8$CO— wherein R$^8$ is selected from the group consisting of: hydrogen, alkyl of 1–12 carbon atoms, aryl, substituted aryl, aralkyl and fluoroalkyl.

12. The thin film transistor device of claim 11, wherein said adduct is hydrolyzed to form a compound represented by the formula:

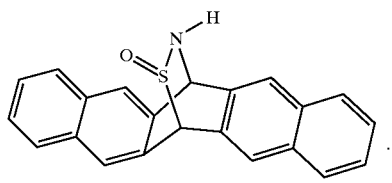

13. The thin film transistor device of claim 2, wherein said dienophile is an azodicarboxylate compound represented by the formula:

RO—CO—N=N—COOR and wherein said adduct is represented by the formula:

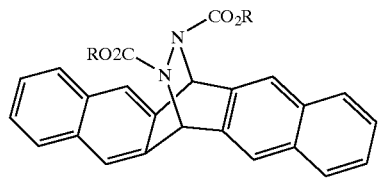

and
wherein R is selected from the group consisting of: alkyl of 1–12 carbon atoms, aryl, aralkyl, chloroalkyl, fluoroalkyl and substituted aryl having a substituent selected from the group consisting of: —F, —Cl, —Br, —NO$_2$, —CO$_2$R, trialkylsilyl and acyl; wherein said acyl is represented by the formula: R$^8$CO— wherein R$^8$ is selected from the group consisting of: hydrogen, alkyl of 1–12 carbon atoms, aryl, substituted aryl, aralkyl, chloroalkyl and fluoroalkyl.

14. The thin film transistor device of claim 13, wherein R is selected from the group consisting of: benzyl, alkyl of one to five carbon atoms, partially or fully chlorinated alkyl of one to four carbon atoms and partially or fully fluorinated alkyl of one to four carbon atoms.

15. The thin film transistor device of claim 13, wherein said adduct is hydrolyzed to form a cyclic diamine compound represented by the formula:

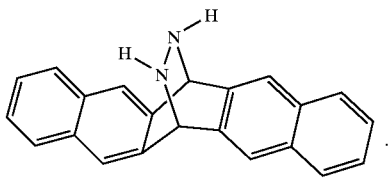

16. The thin film transistor device of claim 15, wherein said adduct is oxidized to give an azo compound represented by the formula:

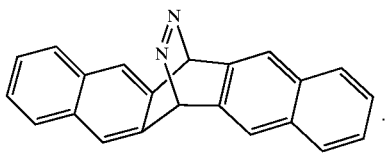

17. The thin film transistor device of claim 2, wherein said polycyclic aromatic compound is selected from the group consisting of: oligothiophene, perylene, benzo[ghi]perylene and coronene.

18. The thin film transistor device of claim 1, wherein said substrate is selected from the group consisting of: glass, plastic, quartz, metals, highly doped silicon and undoped silicon.

19. The thin film transistor device of claim 18, wherein said plastic is selected from the group consisting of: polyethylene terephthalate, polycarbonate and polyimide.

20. The thin film transistor device of claim 1, wherein said gate electrode is made of a material selected from the group consisting of: chromium, titanium, aluminum, copper, gold, platinum, palladium, conducting polyaniline, conducting polythiophene and conducting polypyrrole.

21. The thin film transistor device of claim 1, wherein a self assembled monolayer comprising a material selected from the group consisting of: alkyl thiol, alkyl phosphonic acid and alkyl hydroxamic acid is applied onto the surface of said source and said drain electrodes.

22. The thin film transistor device of claim 1, wherein said device is heated to a temperature in the range of from about 100° C. to about 250° C. to convert said precursor to said polycyclic aromatic compound.

23. The thin film transistor device of claim 1, wherein said polycyclic aromatic compound precursor is segmented by a process selected from the group consisting of: screen printing, microcontact printing and blanket film patterning to reduce leakage and stray currents in said thin film transistor device.

* * * * *